United States Patent
Thompson

(10) Patent No.: US 12,186,285 B2
(45) Date of Patent: Jan. 7, 2025

(54) COMPOSITIONS AND METHODS OF TREATMENT FOR TINEA PEDIS

(71) Applicant: THERAPEUTICS, INC., San Diego, CA (US)

(72) Inventor: Walter Thompson, San Diego, CA (US)

(73) Assignee: THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 17/466,770

(22) Filed: Sep. 3, 2021

(65) Prior Publication Data

US 2022/0062201 A1 Mar. 3, 2022

Related U.S. Application Data

(60) Provisional application No. 63/074,404, filed on Sep. 3, 2020.

(51) Int. Cl.
*A61K 31/137* (2006.01)
*A61K 31/17* (2006.01)
*A61P 31/10* (2006.01)

(52) U.S. Cl.
CPC ............ *A61K 31/137* (2013.01); *A61K 31/17* (2013.01); *A61P 31/10* (2018.01)

(58) Field of Classification Search
CPC ........ A61K 31/137; A61K 31/17; A61P 31/10
See application file for complete search history.

(56) References Cited

PUBLICATIONS

Kircik et al., Journal of Drugs in Dermatology, vol. 13, No. 2, pp. 162-165 (Feb. 2014).*
Gold et al., Journal of Drugs in Dermatology, vol. 12, No. 8, p. 911, Abstract (Aug. 2013).*

* cited by examiner

*Primary Examiner* — Alicia L Otton
(74) *Attorney, Agent, or Firm* — Nath, Goldberg & Meyer; Joshua B. Goldberg

(57) ABSTRACT

Pharmaceutical compositions containing a synergistic combination of at least one antifungal active ingredient and at least one keratolytic agent and methods of treating tinea pedis with the pharmaceutical compositions are described. These pharmaceutical compositions include synergistic combinations of naftifine or terbinafine and urea, or naftifine or terbinafine and ammonium lactate, for effective treatment of moccasin-type and interdigital-type tinea pedis.

5 Claims, No Drawings

COMPOSITIONS AND METHODS OF TREATMENT FOR TINEA PEDIS

BACKGROUND

Tinea pedis, otherwise known as athlete's foot, is a common, highly contagious fungal skin infection, usually of the foot, caused by a dermatophyte fungus, typically of the *Trichophyton* genus including *T. rubrum* and *T. mentagrophytes* (also known as *T. interdigitale*), but also potentially by *Epidermophyton floccosum*. Dermatophytes are fungi that require keratin for growth. Other forms of tinea, including as non-limiting examples, tinea cruris, tinea corporis, tinea capitis, and tinea versicolor, are similar fungal skin infections of other parts of the body, generally treatable the same way as tinea pedis.

It is estimated more than 12 million people in the United States suffer from tinea pedis each year, and that nearly 70% of the population will be afflicted with this condition at some point in their life. The symptoms of an athlete's foot infection include itching, scaling (often a scaling red rash), and cracking of the skin on the foot caused by progression of the fungal infection through the skin of the foot. The infection frequently starts between the toes and may lead to blisters or ulcers. The infection is typically transmitted in moist communal areas where the fungal agents can be picked up by people walking barefoot, such as in showers or bathhouses, and then requires a warm moist environment (e.g., the inside of a shoe) to incubate. The infection can affect one or both feet and can spread to the subject's hands—especially if they scratch or pick the infected parts of their feet.

Interdigital-type tinea pedis—between the toes—is most common and typically occurs in the fourth and fifth toe web spaces but can spread to all of the toe webs. This type of tinea pedis is characterized by maceration, scaling and itching and is primarily caused by *T. rubrum*, although a variant of interdigital-type tinea pedis is caused by *T. mentagrophytes*.

Patients with moccasin-type tinea pedis suffer from an infection characterized by scaling and thickening buildup of the skin on the sole and sides of the foot—areas that would be typically covered by a moccasin. *T. rubrum* is most commonly associated with moccasin-type tinea pedis. While either foot may be affected, bilateral involvement is most often seen. If left untreated, the skin of the foot can thicken and eventually crack, rendering the patient vulnerable to secondary bacterial infections that can develop to be quite serious.

Moccasin-type tinea pedis is often particularly difficult to successfully treat using topical antifungals alone, at least in part due to the thickness of the scaly buildup on the foot. This makes it difficult for the antifungal to reach the dermatophytes that are beneath the surface of the skin.

In addition, because of the need for a drug treatment to penetrate the thick scaly surface, in vitro tests using cultures of *Trichophyton* species currently cannot provide reliable and accurate results regarding the potential efficacy of topical treatments. For example, while in vitro growth of *Trichophyton* species can provide information regarding the kill potential for an antifungal by assessing the "zone of inhibition" produced after treatment with the antifungal, without the ability to ensure the antifungal can reach the dermatophyte and/or to effectively measure skin penetration, the efficacy of treatment is uncertain at best, depending in large part on the degree of infection and thickening of the skin for a particular patient.

Furthermore, there is no reliable animal model available for moccasin-type tinea pedis, making the testing of new drugs and/or drug combinations in a skin-penetration situation difficult at best. While a few researchers have had some success using a guinea pig animal model (see, for example, Shimamura et al. (2012) J Biomed Biotechnol 2012: 125384), issues remain, and stringent clinical human testing is required to reliably determine the efficacy of a treatment.

Consequently, there remains a need for a safe and effective treatment of tinea pedis, and especially moccasin-type tinea pedis, that will sufficiently treat and/or eliminate the underlying dermatophyte fungus causing the infection, and thus alleviating the discomfort caused by such an infection.

SUMMARY

In one aspect of the invention, pharmaceutical compositions are provided. These compositions contain an antifungal active ingredient, such as an allylamine (e.g., naftifine, terbinafine, butenafine), and/or an azole (e.g., econazole, miconazole), and a synergistically effective amount of a keratolytic agent (e.g., urea, ammonium lactate, salicylic acid, podofilox, podophyllum resin, trichloroacetic acid, alpha-hydroxy acids, poly hydroxyl acids). Additionally, methods of treating moccasin-type tinea pedis and interdigital-type tinea pedis are provided comprising administering a composition comprising synergistically effective combination of an antifungal active ingredient (e.g., allylamine, azole) and a synergistically effective amount of a keratolytic agent (e.g., urea) to a subject in need thereof. These treatments would also generally be expected to treat other forms of tinea including, for example, tinea cruris, tinea corporis, tinea capitis, and tinea versicolor.

DETAILED DESCRIPTION

As used herein, the term "allylamine" refers to a member of a class of antifungal agents that that acts on the inhibition of squalene epoxidase that is principally used for the ergosterol biosynthesis pathway of fungal cell membrane formation.

As used herein, the term "antifungal" refers to a drug or other substance used to treat the fungus, reduce the fungus, kill the fungus, and/or prevent fungal growth.

As used herein, the term "azole" refers to a member of a class of antifungal agents that acts on the inhibition of cytochrome P450 dependent enzyme lanosterol 14-alpha-demethylase, which converts lanosterol to ergosterol, the main sterol in the fungal cell membrane. Azole antifungals are classified either as imidazoles having two nitrogens in the azole ring, or as triazoles having three nitrogens in the azole ring.

As used herein, the term "imidazole antifungal" refers to an azole antifungal having two nitrogens in the azole ring. Examples of imidazole antifungals include: clotrimazole, econazole, ketoconazole, miconazole, and tioconazole.

As used herein, the term "triazole antifungal" refers to an azole antifungal having three nitrogens in the azole ring. Examples of triazole antifungals include: fluconazole, itraconazole, posaconazole, and voriconazole.

As used herein, the term "butenafine" refers to a synthetic benzylamine antifungal similar to the allylamine antifungals. A butenafine works by inhibiting the synthesis of ergosterol by inhibiting squalene epoxidase, an enzyme responsible for the creation of sterols needed in fungal cell membranes.

As used herein, the term "amorolfine" refers to an antifungal similar to the allylamine antifungals. An amorolfine works by inhibiting delta 14-sterol reductase and cholestenol delta-isomerase, which depletes ergosterol and causes ignosterol to accumulate in the fungal cytoplasmic cell membranes.

As used herein, the phrase "emulsifying wax" refers to a vegetable- or petroleum-based wax treated with a detergent to cause it to make oil and water bind together into a smooth emulsion. The phrase "emulsifying wax NF" refers to cetearyl alcohol and a polyoxyethylene derivate of a fatty acid ester of sorbitan (a polysorbate).

As used herein, the phrase "light mineral oil" refers to a mixture of liquid hydrocarbons from petroleum, typically with a specific gravity of 0.818-0.880.

As used herein, the phrase "keratolytic" or "keratolytic agent" refers to a topical compound which, when applied to the skin, causes thinning of the skin under and around the application. Keratolytics can also soften keratin, a major component of the skin, for example by swelling and hydrolyzing the skin. Examples of topical keratolytics include, without limitation: urea, ammonium lactate, salicylic acid, podofilox, podophyllum resin, trichloroacetic acid, alpha-hydroxy acids, poly hydroxyl acids, lactic acid, allantoin, resorcinol, and glycolic acid.

As used herein, the phrase "synergistic effect" refers to an interaction between two or more drugs and/or active pharmaceutical ingredients that causes the total effect of the drugs and/or ingredients to be greater than the sum of the individual effects of each drug or active pharmaceutical ingredient if they were applied separately.

As used herein, the phrase "about" when applied to a particular amount, such as for example "about 1.0 wt %," refers to the specified amount ±20%. Accordingly, a recitation of "about 1.0 wt %" refers to a range of 0.80 to 1.2 wt %.

As used here, recitation of a "%" of a composition ingredient refers to the weight percent, or wt %, of that ingredient in relation to the composition as a whole. Thus, for example, a composition with "1.3% naftifine" means 1.3 wt % naftifine relative to the composition.

As used herein, a formulation with pharmaceutically acceptable stability is a formulation where physicochemical stability attributes remain within specifications for at least 24 months when stored at room temperature. These attributes include, but are not limited to, assay of the active pharmaceutical ingredients, degradation products, pH, viscosity, appearance, and bulk homogeneity.

As used herein, "desirable cosmetic attributes" include, but are not limited to, an easy to spread topical formulation at the treatment site, ease of rub-in and absorption into the skin, lack of sticky or chalky residue, and fast drying (or dry-down) at the application site.

As used herein, the term "KOH" refers to a potassium hydroxide microscopy examination of a tissue sample taken from a patient. A skin lesion KOH exam is a simple test conducted, usually by a doctor, on skin scrapings from a patient's problem area to diagnose the presence or absence of a fungal infection of the skin. The potassium hydroxide destroys non-fungal skin cells, so that any fungal cells that may be present can be observed under a microscope.

As used herein, the phrase "complete cure" means the subject is completely cured from the tinea infection, such as a tinea pedis fungal infection. A complete cure of moccasin-type tinea pedis, for example, may be indicated by a negative KOH result, negative fungal culture results, and no evidence of moccasin-type tinea pedis-induced erythema, scaling, or pruritus. Oftentimes a four-point severity scale of 0 (none), 1 (mild), 2 (moderate), and 3 (severe) is used to score erythema, itch, and scaling. Similarly, a "complete cure" from interdigital-type tinea pedis may be indicated by a negative KOH result, negative fungal culture results, and no evidence of interdigital-type tinea pedis-induced erythema, scaling, or pruritus.

As used herein, the phrase "effective treatment" for a patient who had moccasin-type tinea pedis means the subject has a negative KOH result, negative fungal culture results, and no to mild moccasin-type tinea pedis-induced erythema and/or scaling, with no pruritus. Similarly, "effective treatment" for a patient who had interdigital-type tinea pedis means the subject has a negative KOH result, negative fungal culture results, and no to mild interdigital-type tinea pedis-induced erythema and/or scaling, with no pruritus.

As used herein, the phrase "mycological cure" means the subject has a negative KOH result, or other negative fungal results.

The pharmaceutical compositions of the invention contain a therapeutically effective amount of one or more antifungal compounds. One class of antifungal compounds is the allylamines, which includes naftifine, terbinafine, and which is considered herein to encompass butenafine and amorolfine, and combinations thereof. The allylamine compounds may be present in the form of a pharmaceutically acceptable salt. Suitable pharmaceutically acceptable salts are known in the art (see, for example, Berge et al. (1977) *J. Pharm. Sci.* 66(1):1-19). Commonly used pharmaceutically acceptable salts include hydrochloride, hydrobromide, sulphate, phosphate or acid phosphate, acetate, maleate, fumarate, lactate, tartrate, citrate, or gluconate. Oftentimes the pharmaceutically acceptable salt is hydrochloride.

A second class of antifungal compounds are the azoles, which include imidazoles and triazoles. Examples of imidazoles are, without limitation: clotrimazole, econazole, ketoconazole, miconazole, and tioconazole. Examples of triazoles include, without limitation: fluconazole, itraconazole, posaconazole, and voriconazole. In some instances, one or more imidazoles may be used in combination with one or more triazoles. In other instances, one or more azole antifungals are present in combination with one or more allylamine or other antifungal agents.

Similar to the allylamine antifungal compounds, the azole compounds may be present in the form of a pharmaceutically acceptable salt. Suitable pharmaceutically acceptable salts are known in the art (see, for example, Berge et al. (1977) *J. Pharm. Sci.* 66(1):1-19). Commonly used pharmaceutically acceptable salts include hydrochloride, hydrobromide, sulphate, phosphate or acid phosphate, acetate, maleate, fumarate, lactate, tartrate, citrate, or gluconate. Oftentimes the pharmaceutically acceptable salt is hydrochloride.

The antifungal active ingredient(s) may be present individually or jointly in any suitable amount, such as from 0.10 wt % to 2.25 wt %; 0.10 wt % to 0.50 wt %; 0.10 wt % to 0.75 wt %; 0.2 wt % to 1.3 wt %; 0.3 wt % to 1.5 wt %; 0.4 wt % to 1.8 wt %; 0.60 wt % to 2.0 wt %; 0.70 wt % to 2.0 wt %; 0.75 wt % to 1.3 wt %; 1.0 wt % to 2.0 wt %; 1.3 wt % to 1.8 wt %; or at about any single value within the range, for example, at about 0.1, 0.2, 0.25, 0.3, 0.4, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9, 2.0, 2.1, 2.2, 2.25, or 2.3 wt %. All wt % figures reflect wt % relative to the composition taken as a whole. All specific numbers are intended to reflect the specified amount, ±20%. Accordingly, a recitation of 1.0 wt % (or "about 1.0 wt %," as defined above) is intended to reflect a range of 0.8 to 1.2 wt %.

Certain embodiments of the pharmaceutical composition and method include naftifine hydrochloride as the antifungal active ingredient, in a pharmaceutically acceptable amount; that is, an amount sufficient to provide the desired antifungal and curative effect. In some embodiments, the antifungal active ingredient is naftifine hydrochloride, present, for example, in an amount between about 0.5 wt % and 2 wt %, or about any single value within that range, for example about 0.5, 0.6, 0.7, 0.8, 0.9, 1.0, 1.1, 1.2, 1.3, 1.4, 1.5, 1.6, 1.7, 1.8, 1.9, or 2.0 wt %, preferably in an amount of about 1.0 wt % or an amount of 1.3 wt %.

The pharmaceutical compositions of the invention also contain a therapeutically effective amount of one or more keratolytic agents. The keratolytic(s) act to cause thinning of the skin over, under and around the site of topical administration, but can also soften keratin, a major component of the skin, for example by swelling and hydrolyzing the skin. Examples of topical keratolytics include, without limitation: urea, ammonium lactate, salicylic acid, podofilox, podophyllum resin, trichloroacetic acid, alpha-hydroxy acids, poly hydroxyl acids, lactic acid, allantoin, resorcinol, and glycolic acid. Typically, the keratolytic is present in the formulation in an amount of from 10 wt % to 45 wt %, or from 20 wt % to 30 wt %, or 25 wt % to 35 wt %, 30 wt % to 45 wt %, or at about any single value within the range, for example, at about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 wt %. Again, as throughout this application, all wt % figures reflect wt % relative to the composition taken as a whole. All specific numbers are intended to reflect the specified amount, ±20%. Accordingly, a recitation of 10 wt % (or "about 10 wt %") is intended to reflect the range of 8 to 12 wt %.

The pharmaceutical compositions of the invention contain a synergistically effective combination of at least one antifungal active ingredient and at least one keratolytic. A "synergistically effective" combination of two components, as defined above, means an amount of each component such that the combination of the antifungal active ingredient and keratolytic is more effective, as measured by the percent of subjects achieving complete cure, effective cure, or mycological cure after treatment duration, as compared to the sum of the effectiveness of the antifungal agent alone and keratolytic alone. However, due to the nature of pharmaceutical treating agents, the synergistic effect from the combination of the antifungal active ingredient and the keratolytic may require more than simply combining effective amounts of these two ingredients together. That is, the synergistic effect may require a particular ratio of those ingredients in order to maximally achieve a significant clinical benefit from the combination. Too small of an amount of either ingredient will not provide sufficient activity, while too much of either agent may effectively already maximize the intended effect, thereby muting the potential synergy from the combination. Ideally, and in order to minimize exposure of the subject to excessive amounts of the treating agents, smaller amounts would be used that together provide synergistic results that achieve the intended purpose of the treatment.

As an example, urea is a naturally occurring humectant and keratolytic that has been used safely and effectively to treat a variety of dermatological disorders, including pruritus, eczema, dry skin, hyperkeratosis, and xerosis. Urea has also been used in combination with various antifungal medications in the treatment of onychomycosis and various types of tinea including tinea pedis, such as interdigital-type or moccasin-type tinea pedis. In one aspect of the composition of the invention, urea is present in an amount that is effective to synergistically interact with the antifungal active ingredient. Typically, urea is present in the formulation in an amount of from 10 wt % to 40 wt %, such as from 20 wt % to 30 wt % or 25 wt % to 35 wt %, or at about any single value within the range, for example, at about 20, 21, 22, 23, 24, 25, 26, 27, 28, 29, 30, 31, 32, 33, 34, 35, 36, 37, 38, 39, or 40 wt %. Again, all wt % figures reflect wt % relative to the composition taken as a whole. All specific numbers are intended to reflect the specified amount, ±20%. Accordingly, a recitation of 30 wt % (or "about 30 wt %") is intended to reflect the range of 24 to 36 wt %.

In one specific embodiment, urea is combined with naftifine hydrochloride at a ratio of 30 wt %:1.3 wt %, relative to the composition, providing a clinically, statistically significant synergistic response. However, in another embodiment, a ratio of 20 wt % urea:0.7 wt % naftifine also may be used to provide a synergistic effect.

In one embodiment of the present invention, the composition further comprises other dermatologically acceptable excipients, such as one or more of the following: emollients (e.g., lanolin, liquid paraffin, mineral oil, dimethicone, long chain fatty acid esters, isopropyl myristate), humectants (e.g., propylene glycol, hyaluronic acid, silicones, sugar polyols), solvents (e.g., water, vegetable or animal oils, silicones, alcohols, glycerol, dimethyl isosorbide), emulsifiers (e.g., polysorbates, laureth-4, potassium cetyl sulfate, tragacanth, sodium lauryl sulfate, glyceryl monooleate), surfactants (e.g., sodium stearate, docusate, alkyl ether phosphates, sulfonates, phosphate esters), penetration enhancers (e.g., pyrrolidones, methyl laurate, saturated or unsaturated fatty acid or ester thereof, sulfoxides), structuring agents (e.g., hydrogenated vegetable glycerides, polymeric waxes, beeswax), and viscosity modifiers (e.g., carbomer, celluloses, taurine, betaine, theanine, citrulline, sarcosine). Some excipients are known in the art to have more than one function. As an example, without limitation, some emollients can act as penetration enhancers and some penetration enhancer scan serve as emollients.

Suitable polyols preferably have between 2 and 8 carbon atoms, such as glycerin, propylene glycol, and sorbitol. They may be present, individually or in combination, in any amount that will result in a stable formulation with desirable cosmetic properties, for example from 1 wt % to 15 wt %, from 2 wt % to 12 wt %, or from 3 wt % to 10 wt %. One embodiment of the formulation contains glycerin and sorbitol, for example 6 wt % glycerin and 3 wt % sorbitol.

Emollients promote skin softness and smoothness, and can also have other effects such as helping to stabilize or emulsify the composition. Excipients that have emollient properties include silicones such as dimethicone, triglycerides, and long chain fatty acid esters such as methyl laurate and glyceryl monooleate. Some embodiments of the invention contain multiple emollients, for example dimethicone, glyceryl monooleate, and methyl laurate. These excipients may be present individually or in combination in amounts ranging from 1 wt % to 20 wt %, from 2 wt % to 18 wt %, from 4 wt % to 15 wt %, from 1 wt % to 15 wt %, from 2 wt % to 12 wt %, or from 3 wt % to 10 wt %. One embodiment of the invention contains 5 wt % dimethicone, 1.75 wt % glyceryl monooleate, and 0.25% methyllaurate as emollients.

Other excipients may be used in a manner known to those of skill in the art to provide a formulation having the desired viscosity and feel, and/or to ensure the other components of the formulation remain in solution or suspension. Such excipients include, for example, mineral oil, especially light mineral oil, as a viscosity modifier and emollient in amounts up to 10 wt %, 5 wt %, or 4 wt %; dimethyl isosorbide as a solvent and penetration enhancer in amounts up to 10 wt %, 3 wt %, or 1 wt %; water as a solvent in amounts up to 50 wt %, up to 40 wt %, or 35 wt %; and emulsifying wax, available commercially, for example including but not limited to POLAWAX™ NF brand self-emulsifying wax (Croda), in amounts up to 25 wt %, up to 15 wt %, or 9 wt %.

Many pH modifiers and buffers are known in the art, such as 28-30% ammonium hydroxide. This modifier has the potential to slow potential degradation of urea by a common-ion effect. Typically, the pH is adjusted to 7.5-10 by addition of the pH modifier. In some cases, during compounding, the pH modifier is added as needed to obtain a pH of 8.0. In other cases, the pH modifier is added as needed during compounding to obtain a pH of 9.0.

Exemplary Preparation

The composition can be prepared using methods known in the art for preparing cream-based compositions. One method of preparing the composition of the invention has the following steps:
(a) Adding emulsifying wax, isopropyl myristate, light mineral oil, dimethicone, methyl laurate, and glyceryl monooleate to a main mixing vessel. After these components are added, this oil phase mixture is warmed to 70-75° C.
(b) Separately, 90% of the required purified water is added to a secondary vessel along with sorbitol, glycerin, and dimethyl isosorbide. Heating and mixing begin with the secondary vessel and the contents are warmed to 70-75° C. before addition of urea. These water-based ingredients are mixed until all of the desired keratolytic(s) and/or combinations thereof, such as urea, have completely dissolved. Heating and mixing are then discontinued with the secondary vessel.
(c) The desired antifungal ingredient(s) and/or combinations thereof, such as naftifine hydrochloride, are added to the main mixing vessel and dispersed completely.
(d) The aqueous phase from the secondary vessel is transferred to the main vessel. The combined oil and water-phase contents are mixed for a suitable duration to provide a uniform mixture, for example, about 10 minutes at 70-75° C. before heating is discontinued.
(e) The main vessel contents are then mixed with a high shear homogenization for 10 minutes, or until a uniform emulsion has been prepared.
(f) Homogenization is then discontinued, and the contents of the main vessel are mixed while the pH is adjusted to approximately 8.0 with ammonium hydroxide. The batch weight is then brought to target with purified water. The batch is mixed further until the temperature is below 40° C.
(g) The finished bulk drug product is cooled to room temperature before filling into a suitable pharmaceutical container closure system (e.g., a tube, an airless pump, a jar)

Treatment analysis and performance of the finished drug product is best conducted in human subjects suffering from the disease. However, in some instances, the finished drug product can be tested without the participation of living subjects. For example, cadaver skin has been used for analysis of penetration of some antifungal preparations (see, for example, Ceschin-Roques et al. (1991) Skin Pharmacol. 4(2):95-9; Hanel et al. (1988) Ann N Y Acad Sci 544:329-37; US 201002269983A1), although these procedures are not particularly robust or dependable for many drug formulations. A recent promising alternative is the EPISKIN™ brand human skin model, a reconstructed human epidermis (see Liang et al. (2016) Chinese Medical Journal 129(1): 54-58; Corzo-Leon et al. (2019) Front Microbiol 10:1172). These references are incorporated by reference herein in their entirety and the protocols and procedures set forth in them can be used for analysis of the drug products and formulations of the invention.

The invention also provides a method of treating tinea pedis in a subject in need of such treatment by administering a composition of the invention to the subject at the site of infection and/or about 1 inch beyond the margin of the affected areas of the foot. Various treatment regimens may be used according to the needs of the specific patient. In one embodiment of the invention the composition is applied to the affected areas of the feet once, twice, three times, or four times daily. In one embodiment the composition is applied twice per day. Treatment is continued until a desired therapeutic effect (e.g., complete cure, effective cure, or mycological cure) is achieved, for example for one week, two weeks, three weeks, or four weeks. In one embodiment of the invention the composition is applied twice daily, in the morning and evening. In another embodiment of the invention the composition is applied twice daily for two weeks.

EXAMPLES

In each of the following examples, the formulations were prepared using the exemplary preparation method described above. For formulations that contain naftifine hydrochloride without urea, or urea without naftifine hydrochloride, the omitted ingredient was substituted with purified water, but the preparation was otherwise the same.

The effects of treatment were analyzed, in part, using a KOH test. KOH is one of the main methods of detecting fungal infections, as when the strong alkali is mixed with a skin sample from the affected or suspected area, it softens, digests, and clears the keratin skin tissues so that the fungus, if present, can be easily seen under a microscope. The technique is well known in the art, and generally involves placing a drop of about 20% KOH solution on a slide (in these examples Chlorazol Black E containing KOH was used), transferring the skin sample to the drop, and covering the sample with glass. After the KOH has cleared the keratin from the sample, it is examined microscopically to determine if fungus is present.

Clinical Testing in Human Subjects

A study investigated 2 different naftifine strengths of UHE-103 cream: low dose combination UHE-103A1B (1.3% naftifine/30% urea) and high dose combination UHE-103A2B (1.8% naftifine/30% urea) compared to their monads: low dose naftifine UHE-103A1 (1.3%) or high dose naftifine UHE-103A2 (1.8%) as the sole active ingredient, respectively, and UHE-103B (urea, 30% and no naftifine) in 240 subjects with moccasin-type tinea pedis with at least moderate scaling confirmed by a positive KOH and a fungal culture positive for a dermatophyte.

Subjects were randomized 1:1:1:1:1 to the following treatment groups:
1. UHE-103A1 (naftifine hydrochloride) cream, 1.3%
2. UHE-103A2 (naftifine hydrochloride) cream, 1.8%
3. UHE-103B (urea) cream, 30% (Control)

4. UHE-103A1B (naftifine hydrochloride and urea) cream, 1.3%/30%
5. UHE-103A2B (naftifine hydrochloride and urea) cream, 1.8%/30%

The subjects applied the cream twice daily to all affected areas of both feet, once in the morning and once in the evening, for two weeks. All subjects were then evaluated for Complete Cure, Effective Treatment, and Mycological Cure 43 days after the beginning of the study.

As seen in Table 1, the low dose combination UHE-103A1B cream achieved a significantly higher Complete Cure rate (21.4%) compared to both of its individual monads: the low dose naftifine monad UHE-103A1 (8.3%, p=0.027) and the urea monad UHE-103B (0%, p=0.006) at Day 43. These results were further supported with similar findings for Effective Treatment and Mycological Cure.

As seen in Table 2, the high dose combination UHE-103A2B cream did not achieve a statistically significantly higher Complete Cure rate (19.4%) on day 43 compared to the high dose naftifine monad UHE-103A2 (25%, p=0.701). Even so, 19.4% of subjects treated with this high dose combination formulation achieved a Complete Cure. These results provided similar comparisons to the high dose naftifine monad for Effective Treatment (41.7%, p=0.876) and for Mycological Cure (66.7%, p=0.444). However, compared to the urea monad at day 43, the high dose combination result was statistically significantly higher for all three thresholds: the Complete Cure rate (0%, p=0.01), the Effective Treatment rate (0%, p<0.001), and the Mycological Cure rate (9.1%, p<0.001).

As seen in Table 3, the low dose combination UHE-103A1B also achieved higher cure rates than the high dose combination UHE-103A2B in all three endpoints—Complete Cure, Effective Treatment, and Mycological Cure at day 43. Even so, both formulations were effective in curing moccasin-type tinea pedis.

TABLE 1

Efficacy Results For UHE-103A1B vs Monads at Day 43

| Endpoint | UHE-103A1B (1.3%/30%) | UHE-103A1 (1.3%) | UHE-103B (30%) |
|---|---|---|---|
| Complete Cure | 21.4% | 8.3% | 0 |
| p value vs. matched dose naftifine monad | 0.027 | | |
| p value vs. urea monad | 0.006 | | |
| Effective Treatment | 42.9% | 16.7% | 0 |
| p value vs. matched dose naftifine monad | 0.005 | | |
| p value vs. urea monad | <0.001 | | |
| Mycological Cure | 60.7% | 38.9% | 9.1% |
| p value vs. matched dose naftifine monad | 0.044 | | |
| p value vs. urea monad | <0.001 | | |

TABLE 2

Efficacy Results for UHE-103A2B vs Monads at Day 43

| Endpoint | UHE-103A2B (1.8%/30%) | UHE-103A2 (1.8%) | UHE-103B (30%) |
|---|---|---|---|
| Complete Cure | 19.4% | 25% | 0 |
| p value vs. matched dose naftifine monad | 0.701 | | |
| p value vs. urea monad | 0.01 | | |
| Effective Treatment | 38.7% | 41.7% | 0 |
| p value vs. matched dose naftifine monad | 0.876 | | |
| p value vs. urea monad | <0.001 | | |
| Mycological Cure | 58.1% | 66.7% | 9.1% |
| p value vs. matched dose naftifine monad | 0.444 | | |
| p value vs. urea monad | <0.001 | | |

TABLE 3

Efficacy Results for UHE-103A1B and UHE-103A2B at Day 43

| Endpoint | UHE-103A1B (1.3%/30%) | UHE-103A2B (1.8%/30%) |
|---|---|---|
| Complete Cure | 21.4% | 19.4% |
| p value vs. matched dose naftifine monad | 0.027 | 0.701 |
| p value vs. urea monad | 0.006 | 0.010 |
| Effective Treatment | 42.9% | 38.7% |
| p value vs. matched dose naftifine monad | 0.005 | 0.876 |
| p value vs. urea monad | <0.001 | <0.001 |
| Mycological Cure | 60.7% | 58.1% |
| p value vs. matched dose naftifine monad | 0.044 | 0.444 |
| p value vs. urea monad | <0.001 | <0.001 |

In the same clinical study, 22 subjects treated with UHE103A1B at baseline had concurrent evidence of interdigital-type tinea pedis. At Week 6/Day 43, 5 subjects (23.8%) exhibited clinical clearing of their interdigital disease. These findings demonstrate that UHE103A1B can also be effective for treating interdigital-type tinea pedis.

While the present invention has been disclosed in this patent application by reference to details of various embodiments of the invention, it is to be understood that the disclosure is intended to be illustrative rather than limiting. It is contemplated that many alternatives, modifications, and variations thereof will be apparent to those of ordinary skill in the art. All such alternatives, modifications, and variations are intended to fall within the spirit of the present invention and the scope of the appended claims.

All publications, databases, GenBank sequences, patents and patent applications cited in this Specification are herein incorporated by reference as if each was specifically and individually indicated to be incorporated by reference.

What is claimed is:

1. A method for treating tinea pedis in a subject, the method comprising administering an effective amount of a pharmaceutical composition to a subject in need thereof, wherein the pharmaceutical composition comprises a synergistic combination of at least one antifungal active ingredient that includes 1.3% naftifine hydrochloride and 30% of a keratolytic agent including urea.

2. The method of claim 1, wherein the subject is being treated once daily for moccasin-type tinea pedis.

3. The method of claim 1, wherein the subject is being treated once daily for interdigital-type tinea pedis.

4. The method of claim 1, wherein the pharmaceutical composition is administered once or twice daily for at least two weeks for moccasin-type tinea pedis.

5. A method for treating tinea in a subject, the method comprising administering an effective amount of a pharmaceutical composition to a subject in need thereof, wherein the pharmaceutical composition comprises a synergistic combination of at least one antifungal active ingredient that includes 1.3% naftifine hydrochloride and 30% of a keratolytic agent including urea.

* * * * *